(12) United States Patent
Ibert et al.

(10) Patent No.: US 11,168,152 B2
(45) Date of Patent: Nov. 9, 2021

(54) HYDROGENATED GLUCOSE POLYMER COMPOSITION CONTAINING DIETARY FIBRES

(71) Applicant: ROQUETTE FRERES, Lestrem (FR)

(72) Inventors: Mathias Ibert, La Chapelle d'Armentieres (FR); Baptiste Boit, La Gorgue (FR)

(73) Assignee: ROQUETTE FRERES, Lestrem (FR)

( * ) Notice: Subject to any disclaimer, the term of this patent is extended or adjusted under 35 U.S.C. 154(b) by 377 days.

(21) Appl. No.: 16/315,706

(22) PCT Filed: Jun. 9, 2017

(86) PCT No.: PCT/FR2017/051462
§ 371 (c)(1),
(2) Date: Jan. 7, 2019

(87) PCT Pub. No.: WO2018/007697
PCT Pub. Date: Jan. 11, 2018

(65) Prior Publication Data
US 2019/0300626 A1    Oct. 3, 2019

(30) Foreign Application Priority Data

Jul. 8, 2016 (FR) .................... 1656604
Feb. 28, 2017 (FR) .................... 1751618

(51) Int. Cl.
| | |
|---|---|
| C08B 30/00 | (2006.01) |
| C08B 30/18 | (2006.01) |
| A23L 29/30 | (2016.01) |
| A61K 31/70 | (2006.01) |
| A61K 31/75 | (2006.01) |
| A61K 47/36 | (2006.01) |
| C08L 3/02 | (2006.01) |

(52) U.S. Cl.
CPC .............. *C08B 30/18* (2013.01); *A23L 29/30* (2016.08); *A61K 31/70* (2013.01); *A61K 31/75* (2013.01); *A61K 47/36* (2013.01); *C08L 3/02* (2013.01)

(58) Field of Classification Search
None
See application file for complete search history.

(56) References Cited

U.S. PATENT DOCUMENTS

| | | | |
|---|---|---|---|
| 4,622,233 A | 11/1986 | Torres | |
| 5,424,418 A * | 6/1995 | Duflot | ................. C08B 37/0009 127/38 |
| 5,573,794 A * | 11/1996 | Duflot | .................... A23G 3/346 127/46.2 |
| 2003/0096055 A1* | 5/2003 | Fuertes | ................... C08B 31/00 426/661 |

FOREIGN PATENT DOCUMENTS

| | | |
|---|---|---|
| EP | 0368451 A2 | 5/1990 |
| EP | 0485304 A2 | 5/1992 |
| EP | 0516491 A2 | 12/1992 |
| EP | 0530111 A1 | 3/1993 |
| FR | 2668147 A1 | 4/1992 |
| WO | 9214761 A1 | 9/1992 |
| WO | 9936442 A1 | 7/1999 |

OTHER PUBLICATIONS

The English translation of the International Search Report, dated Oct. 16, 2017, in the corresponding PCT Appl. No. PCT/FR2017/051462.

* cited by examiner

*Primary Examiner* — Stefanie J Cohen

(57) ABSTRACT

The invention relates to a hydrogenated glucose polymer composition having a total fibre content of more than 50% as determined by the AOAC 2001.03 method, and a dry weight reducing sugar content, SR, lower than 800 ppm. The invention also relates to a method for producing said composition. The invention is also directed to a food or pharmaceutical product comprising said composition.

26 Claims, No Drawings

HYDROGENATED GLUCOSE POLYMER COMPOSITION CONTAINING DIETARY FIBRES

CROSS-REFERENCE TO RELATED APPLICATIONS

This application is a National Stage Application of PCT/FR2017/051462 filed Jun. 9, 2017, which claims priority from French Patent Application Nos. 1656604, filed on Jul. 8, 2016 and 1751618 filed on Feb. 28, 2017. The priority of said PCT and French Patent Applications are claimed. Each of the prior mentioned applications is hereby incorporated by reference herein in its entirety.

SUBJECT OF THE INVENTION

The invention relates to a novel composition of hydrogenated glucose polymers containing dietary fiber and comprising a very low reducing sugar content. Another subject of the invention relates to a process for producing this composition, said process comprising a combination of specific steps of hydrogenation and alkalinization, making it possible to very greatly reduce the amount of reducing functions of the glucose polymer, while only very slightly degrading the structure thereof. Another subject of the invention is a food or pharmaceutical product comprising said composition.

PRIOR ART

Glucose polymers are commonly used in numerous industries such as the food or pharmaceutical industries.

The most common glucose polymers are starch hydrolysates. Starch hydrolysates are generally grouped into two large families, maltodextrins and glucose syrups. Membership of one or the other of these families is determined by their dextrose equivalent (DE), DE being the ratio of the number of reducing sugars to the number of total sugars, multiplied by 100. Maltodextrins have a DE of less than 20, and glucose syrups have a DE of 20 or more.

A starch hydrolysate is essentially digestible and does not comprise dietary fiber.

According to the present invention, "dietary fiber" is intended to mean glucose polymer structures that are not, or are only very slightly, digested by humans.

There are other glucose polymers containing nondigestible dietary fiber. While starches and starch hydrolysates solely have glucide bonds of α-1,4 and α-1,6 type, glucose polymers containing nondigestible dietary fiber comprise atypical bonds of 1,2 type (α or β anomerism) and of 1,3 type (α or β anomerism) or else atypical bonds of β-1,4 and β-1,6 type. All of these atypical bonds are not hydrolyzed, or are only hydrolyzed with great difficulty, by human digestive enzymes.

These glucose polymers containing dietary fiber are generally produced by a heat treatment of a starch or of a starch hydrolysate, the hydrolysate which may be used for the production especially being able to be, or comprise, glucose and/or maltose. This heat treatment is carried out using acid or enzymatic catalysis; it enables the formation of the abovementioned atypical bonds and results in the formation of glucose polymers containing dietary fiber.

The abovementioned glucose polymers comprise terminal reducing sugars, which are the most reactive functions of the glucose polymer. Generally speaking, the reducing sugar is considered to be the main element responsible for the thermal instability of the polymers. It is especially this reducing sugar which is liable to react with nitrogen-containing species and lead to Maillard reactions.

Thus, in order to make glucose polymers more thermally stable, it is known to hydrogenate the reducing function of starch hydrolysates, as described in application WO 99/36442 which more particularly describes a process for hydrogenation of a malto-oligosaccharide under sufficiently "mild" conditions so as not to degrade the malto-oligosaccharide. This reaction is preferentially carried out using a catalyst of activated nickel type. Advantageously, the hydrogenation step is carried out at a temperature ranging from 110 to 120° C. and at a pressure ranging from 400 to 700 psi. This document also teaches carrying out the hydrogenation reaction at a pH ranging from 5.0 to 6.0. The resulting malto-oligosaccharide has an "essentially zero" DE, that is to say, according to this document, a DE of at most 1. The glucose polymer does not contain dietary fiber and the reducing sugar content is not indicated.

Moreover, since the preparation of glucose polymers containing dietary fiber comprises a step of heat treatment, these polymers, unlike the starch hydrolysates described above, generally have a problem of coloration. This problem of coloration may be greater when the heat treatment is carried out at high temperature, for example at a temperature exceeding 100° C. Phenomena of coloration are conventionally attributed to the presence of unsaturated bonds. These unsaturated bonds may be those of the reducing glucoses or unsaturated bonds within the polymer (for example alkenes), formed during the heat treatment step.

This problem of coloration of glucose polymers containing dietary fiber may be limited either by using mild preparation conditions as described in document EP 530.111, or by carrying out purification on cationic and anionic resins or with carbon black, as described in documents EP 485.304 and EP 516.491. Another solution is described in U.S. Pat. No. 4,622,233, in which decoloration of the glucose polymer is carried out by peroxides or chlorites.

Another solution for decoloring the product consists in hydrogenating the glucose polymer containing dietary fiber. This hydrogenation was especially described in patent application WO 92/14761. The hydrogenated polydextrose has an "essentially zero" DE, that is to say, according to this document, a DE of less than 1. This document describes the hydrogenation of a polydextrose in a step consisting in heating in the presence of a hydrogenation catalyst and dihydrogen ("hydrogen" in the remainder of the description). Under the conditions of example 9, the polydextrose is formed as a solution with a solids content of 40% with a pH equal to 6.2, and this solution, also comprising Raney nickel, is brought to 140-150° C. under a hydrogen pressure of 1400 psig for 90 minutes. The hydrogenated polydextrose obtained has an amount of reducing sugars of 0.2%. This document also describes a hydrogenation using a borohydride as reducing agent. Under the conditions of example 20, in which the amount of reducing sugars was determined, this amount is 0.4%. These hydrogenated glucose polymers are presented as having an improved color and flavor, while being less reactive with other products comprising amine functions.

U.S. Pat. No. 5,424,418 likewise describes a process for producing a hydrogenated polydextrose comprising the hydrogenation of a polydextrose to form a hydrogenated polydextrose, followed by a step of chromatography of this hydrogenated polydextrose in order to eliminate the sorbitol therefrom. This hydrogenation step is carried out without changing the pH (pH 7 or 8). Very preferentially, the amount of reducing sugars in the product obtained is less than 0.15%. Nonetheless, the examples demonstrate that it not possible to obtain a hydrogenated polymer composition comprising a very low amount of reducing sugars with the process of this document. Even before the chromatography step, the hydrogenated polydextrose comprises a high amount of reducing sugars (in the examples, 0.50%, 0.45% and at least 0.12%) and the subsequent chromatography step does not make it possible to reduce this amount of reducing sugars. Indeed, sorbitol, which is eliminated from the composition during the chromatography step, is not a reducing sugar.

Document EP 654483, in the name of the Applicant, describes, according to one variant, a process in which a hydrogenation step is carried out at a pH of between 4 and 8. More particularly, in example 5, the hydrogenation of a polydextrose that has previously undergone an enzymatic treatment and a treatment with glucose oxidase is described. According to example 5, this hydrogenation is carried out in the presence of Raney nickel on a solution with a solids content of 40% with a pH equal to 7, under a pressure of 50 bar hydrogen. The polydextrose obtained has an amount of reducing sugars of 0.10%, despite the prior use of glucose oxidase, which also makes it possible to reduce the amount of reducing sugars in the composition. The hydrogenation is carried out without modifying the pH during the reaction.

Document EP 368451 also describes, in examples 2 and 10, the hydrogenation of a dextrin that is difficult to digest and which moreover is of higher molecular weight than the polydextrose. This hydrogenation is carried out in the presence of Raney nickel, at 130° C. for 90 minutes or 2 hours, on an aqueous suspension of dextrin with a solids content of 40%, the pH of which is set to 9.5, with a hydrogen pressure of 95 bar. The amount of reducing sugars is not determined, but the Applicant was able to observe that, following this teaching, the amount of reducing sugars was well above 0.1%: it is at least 0.25% and this hydrogenation leads to degradation of the dextrin that is difficult to digest.

Document US 2003/0096055 A1 describes soluble hydrogenated starch derivatives containing fibers that have an improved color and a reducing sugar content reduced by at most 30% compared to the soluble starch derivative before hydrogenation. The sample having the lowest amount of reducing sugars (0.6%) is not according to the invention because it is too low to meet the claimed criteria (reduction of approximately 75%).

Document EP 516491 A2 describes the production of a pyrodextrin hydrolysate comprising several steps of enzymatic treatment and treatment in an autoclave of a pyrodextrin.

Document FR 2 668 147 A1 describes a process for stabilizing an oxidized polysaccharide hydrolysate.

Glucose polymers, whether or not they comprise dietary fiber, are more or less difficult to hydrogenate. Indeed, regardless of the process used, the Applicant was able to observe the following trend: the higher the viscosity of the glucose polymer containing dietary fiber, the more difficult this polymer is to hydrogenate. Since the viscosity of the glucose polymer is mainly linked to its molecular weight, the greater the molecular weight of the glucose polymer, the more difficult it is to reduce the amount of reducing sugars in the composition. Thus, to date, it has never been possible to obtain a hydrogenated glucose polymer composition comprising an amount of reducing sugars by dry weight of less than 1000 ppm using hydrogenation processes.

The products Litesse® Ultra sold by Danisco or Fibersol® 2H sold by Matsutani, which are both hydrogenated glucose polymers containing dietary fiber, comprise (see examples section) respectively 0.15% and 0.25% of reducing sugars.

It emerges from the above that the prior art hydrogenation processes do not make it possible to obtain hydrogenated glucose polymers which comprise a very low amount of reducing sugars. However, even when the amount of reducing sugars is as low as 0.15% or even 0.10%, degradation may occur under the action of heat, especially when the hydrogenated glucose polymer is in the presence of compounds bearing amine functions, with this degradation leading to coloration of the product. However, since these polymers are especially intended for the food industry, it may be necessary to be able to use them under all temperature conditions without excessive browning of the food product comprising them. Since food products have a pH which ranges very generally from 2 to 7, it would be beneficial to be able to provide glucose polymers having improved thermal stability at acid and neutral pH to the food industry. In pharmaceutical applications, it may be necessary for these polymers to be as unreactive as possible with other constituents of a pharmaceutical preparation.

There is therefore a need to obtain novel compositions of hydrogenated glucose polymers containing dietary fiber, which have an even lower amount of reducing sugars than that of compositions that are already known, especially hydrogenated glucose polymers with high molecular weight and containing dietary fiber.

This is precisely the subject of the present invention, which will be described below.

SUMMARY OF THE INVENTION

The invention relates to a hydrogenated glucose polymer composition having a total fiber content, determined according to the AOAC 2001.03 method, of greater than 50% and an amount of reducing sugars by dry weight RS of less than 800 ppm.

Indeed, the Applicant found that it was entirely possible to obtain a hydrogenated glucose polymer composition which has an amount of reducing sugars that had hitherto not been achieved, while only slightly degrading the glucose polymer and while not decreasing, or only very slightly decreasing, the total fiber content in the glucose polymer. The Applicant has achieved this even when the molecular weight of this glucose polymer is high. This composition has numerous advantages and especially little color, little odor, little flavor and excellent temperature-stability, especially from acid to neutral pH. This allows it to be advantageously used in food and pharmaceutical products.

After much research, the Applicant was able to observe that a particular process comprising a first step of hydrogenation of a glucose polymer and a second step of alkalinization made it possible to obtain the hydrogenated glucose polymer composition of the invention.

Therefore, another subject of the invention is a process for producing a hydrogenated glucose polymer composition according to the invention, comprising:
  a step of providing an aqueous solution of glucose polymer containing dietary fiber;
  a step of bringing the aqueous solution into contact with a hydrogenation catalyst in order to provide, optionally after correcting this pH, a solution having a pH ranging from 4 to 7;

a step of hydrogenation of said solution in a reactor for a sufficient duration to achieve a composition, referred to as prehydrogenated composition, having a reducing sugar content ranging from 0.15 to 1%;

followed by a step of modification of the pH of the prehydrogenated composition by addition of a base, said composition having, at the end of this step, a pH ranging from 8.5 to 11;

followed by a step of alkalinization of the prehydrogenated composition, also in the presence of a hydrogenation catalyst and hydrogen, at a temperature of between 100 and 140° C. for a sufficient duration to form the hydrogenated glucose polymer composition.

The process according to the invention has the advantage of only slightly degrading the structure of the glucose polymer. Unlike the processes of the prior art (such as those described in documents U.S. Pat. No. 5,424,418, EP 654483 or WO 92/14761), the process of the invention comprises a step of modification of the pH by addition of a base between the two steps decreasing the amount of reducing sugars in the glucose polymer, i.e. the hydrogenation and alkalinization steps. As demonstrated in the examples section, it is these two steps, carried out at distinct pHs and in this order, which make it possible to obtain the composition of the invention. This is all the more surprising since it is well-known that glucose polymers are relatively unstable at the pH of the alkalinization step. Without wishing to be bound by any theory, it appears that the hydrogenation step makes it possible to make the glucose polymer sufficiently stable in order to be able to effectively subject it to the subsequent alkalinization step and thereby drastically reduce the amount of reducing sugars in the composition of the invention.

The invention will now be described in detail below.

DETAILED DESCRIPTION OF THE INVENTION

A subject of the invention relates to a hydrogenated glucose polymer composition containing dietary fiber and having a very low amount of reducing sugars RS.

"Hydrogenated glucose polymer composition" is intended to mean a composition comprising glucose polymers, the terminal functions of which have been hydrogenated.

The glucose polymer is a glucose polymer containing nondigestible dietary fiber. The composition according to the invention contains a total fiber content, determined according to the AOAC 2001.03 method, of greater than 50%, advantageously greater than 60%, preferably greater than 70%, for example greater than 80%.

There are numerous glucose polymers containing dietary fiber which have been described in the literature. Mention may for example be made of glucose polymers containing dietary fiber obtained by acid catalysis from concentrated aqueous solutions of glucose or glucose syrups, such as those described in documents U.S. Pat. No. 3,876,794 or WO 9841545. The glucose polymers containing dietary fiber may also be obtained from starch, as described for example in documents EP 535627 or EP 538146: reference is then made to nondigestible dextrins.

According to a first preferred variant of the invention, the glucose polymer is the glucose polymer described in document EP 1006128 in the name of the Applicant, that is to say a branched maltodextrin, characterized in that it has between 22% and 35%, preferably between 27 and 34%, of 1->6 glucosidic bonds, a reducing sugar content of less than 20%, a polydispersity index of less than 5 and a number-average molecular weight Mn at most equal to 4500 g/mol.

According to a second preferred variant of the invention, the glucose polymer is the glucose polymer described in document FR 3 032 709 in the name of the Applicant, that is to say a malto-oligosaccharide having a content of α-1,4 bonds of between 70 and 80% of the total number of 1,4-glycosidic bonds.

Glucose polymers containing dietary fiber are also commercially available, for instance Nutriose® sold by the Applicant, Litesse® sold by Danisco, Promitor® sold by Tate and Lyle or else Fibersol®2 sold by Matsutani.

When the glucose polymer contains dietary fiber, it is essential to only slightly degrade the structure of the glucose polymer during the hydrogenation, with a view to retaining the atypical bonds characterizing them and therefore the particular digestibility properties of these products. The invention is therefore particularly beneficial because the process of the invention makes it possible to not, or only slightly, degrade the structure of the glucose polymer and to not, or only slightly, decrease the total fiber content. Surprisingly, this has been made possible by the particular process of the invention, even though it is known that glucose polymers are degraded under basic conditions, which leads, in the case of a glucose polymer containing dietary fiber, to loss of the nutritional advantages associated with this fiber. "Slightly degrade the structure of the glucose polymer" is intended to mean a reduction in the molecular weight Mn of the glucose polymer, during the process for producing the composition of the invention, by proportions not exceeding 10% of the initial molecular weight Mn thereof. "Slightly decrease the total fiber content" is intended to mean a reduction in the total fiber content of the glucose polymer, determined according to the AOAC 2001.03, during the process for producing the composition of the invention, by proportions not exceeding 3%: for example, for a glucose polymer containing 80% fiber, a process has slightly decreased the total fiber content when this content in the hydrogenated composition obtained is no less than 77%.

The hydrogenated glucose polymer composition of the invention has an amount of reducing sugars of less than 800 ppm. This amount is determined by the Nelson-Somogyi method, well-known to those skilled in the art, this method having been the subject of the publication Somogyi M. (1952) J. Biol. Chem., 200 245. For the purposes of the invention, it is necessary to use this Nelson-Somogyi method to determine the amount of reducing sugars in the composition. This is because the other known methods, for example the Bertrand method, do not make it possible to precisely determine the amount of reducing sugars when this amount is as low as that of the compositions of the invention. Preferably, the amount of reducing sugars is less than 700 ppm, for example less than 600 ppm, for example less than 500 ppm, for example less than 400 ppm. The composition according to the invention may have an amount of reducing sugars by dry weight which ranges from 20 to 600 ppm, for example from 50 to 400 ppm.

The composition according to the invention may have, relative to the dry weight of the composition, a dry weight of polyols (DP1H+DP2H) resulting from the hydrogenation of the glucose, of the maltose, and of the isomers thereof, of less than 30%, advantageously less than 25%, for example less than 15%, especially less than 5%, or even less than 2%. This amount may be determined by high-performance liquid chromatography.

According to the invention, the number-average molecular weight Mn of the composition may vary broadly and especially range from 500 to 3000 g/mol, advantageously from 800 to 2600 g/mol. It may for example range from 500 to 1600 g/mol or from 1600 to 2300 g/mol. The weight-average molecular weight Mw of the composition may vary broadly and especially range from 1000 to 6000 g/mol, advantageously from 1300 to 5000 g/mol. It may for example range from 1000 to 3600 g/mol or from 3600 to 6000 g/mol. The molecular weight of the glucose polymer is generally considered to be high when the weight-average molecular weight thereof is greater than or equal to 2500 g/mol. The molecular weights Mn and Mw essentially depend on the molecular weights Mn and Mw of the glucose polymer subjected to the process of the invention. The weight-average molecular weight may be considered to be a decisive factor in terms of the viscosity of the glucose polymer. In practice, the values of Mn and Mw are determined by a measurement method suited to glucose polymers, which may be based on gel permeation chromatography on chromatography columns calibrated with pullulans with known molecular weights. As for the amount RS, this essentially depends on the starting glucose polymer, on the conditions for hydrogenations and on the conditions for alkalinization, which will be described below. The composition according to the invention may have an RS/Mw ratio, RS being expressed as ppm and Mw being expressed as g/mol, ranging from 0.01 to 0.80, especially ranging from 0.02 to 0.60, for example ranging from 0.04 to 0.30.

One subject of the invention relates to a hydrogenated glucose polymer composition having a weight-average molecular weight greater than or equal to 2500 g/mol, for example ranging from 2500 to 6000 g/mol, advantageously ranging from 3600 to 6000 g/mol, or even from 3700 to 5000 g/mol, and an amount RS ranging from 50 to 800 ppm, for example from 80 to 600 ppm, or even from 100 to 400 ppm. This composition is particularly beneficial in that the process of the invention makes it possible to drastically decrease the amount of reducing sugars, even in this variant in which the molecular weight of the glucose polymer is high.

Another subject of the invention relates to a hydrogenated glucose polymer composition having a weight-average molecular weight ranging from 1000 to 3600 g/mol and an amount RS ranging from 30 to 800 ppm, for example from 40 to 500 ppm, or even from 50 to 250 ppm.

The compositions of the invention have improved stability over a broad pH range extending from acid to neutral. This is an advantage in the sense that the vast majority of food products have such a pH. These improved stabilities enable the glucose polymer compositions to be advantageously used in these food products. The treatments are explained in detail in the examples section.

Thus, according to the invention, the hydrogenated glucose polymer composition of the invention has improved stability at acid pH and has, advantageously, after heat treatment of TEST A, an ICUMSA coloration of less than 100, preferentially less than 90, or even less than 70. According to the invention, the hydrogenated glucose polymer composition of the invention has improved stability at neural pH and has, advantageously, after heat treatment of TEST B, an ICUMSA coloration of less than 100, preferentially less than 90, or even less than 70.

The TEST A treatment consists in placing the hydrogenated glucose polymer composition in the form of an aqueous composition buffered at pH=4 and with 25% solids content, then in carrying out a heat treatment of this buffered aqueous composition for 6 hours at 115° C. The TEST B treatment consists in placing the hydrogenated glucose polymer composition in the form of an aqueous composition buffered at pH=7 and with 25% solids content, then in carrying out a heat treatment of this buffered aqueous composition for 6 hours at 85° C.

The composition according to the invention was able to be obtained by a production process comprising:
 a step of providing an aqueous solution of glucose polymer containing dietary fiber;
 a step of bringing the aqueous solution into contact with a hydrogenation catalyst in order to provide, optionally after correcting this pH, a solution having a pH ranging from 4 to 7;
 a step of hydrogenation of said solution in a reactor for a sufficient duration to achieve a composition, referred to as prehydrogenated composition, having a reducing sugar content ranging from 0.15 to 1%;
 followed by a step of modification of the pH of the prehydrogenated composition by addition of a base, said composition having, at the end of this step, a pH ranging from 8.5 to 11;
 followed by a step of alkalinization of the prehydrogenated composition, also in the presence of a hydrogenation catalyst and hydrogen, at a temperature of between 100 and 140° C. for a sufficient duration to form the hydrogenated glucose polymer composition.

The aqueous solution of glucose polymer containing dietary fiber provided may have a solids content ranging from 15 to 40%, for example from 20 to 30%. Those skilled in the art may vary the solids content of the solution according to the glucose polymer and/or the reactor used. The glucose polymers provided depend on the desired hydrogenated glucose polymer composition, especially in terms of Mn, Mw and fiber content. This glucose polymer may have, relative to the dry weight of the composition, a dry weight of sugars (DP1+DP2), that is to say of glucose, maltose, and isomers thereof, of less than 30%, advantageously less than 25%, for example less than 15%, especially less than 5%, or even less than 2%. This amount may be determined by high-performance liquid chromatography. The polymers may be chosen from those described above.

It is possible to prepare the solution of glucose polymer by simply mixing the glucose polymer with water in the desired amounts. The aqueous solution of glucose polymer is brought into contact with a hydrogenation catalyst. Hydrogenation catalysts are known per se; this catalyst may be of Raney nickel type, or any other catalyst for the hydrogenation of sugars may be suitable. Those skilled in the art will know how to adjust the amounts of catalyst to be used; by way of example, use may be made of Raney nickel in amounts that may range from 2 to 10% relative to the dry weight of the glucose polymer, for example approximately 5%.

Before the start of the hydrogenation step, the aqueous solution of glucose polymer has a pH ranging from 4 to 7. This pH may be corrected by adding an acid or a base.

The aqueous solution of glucose polymer is then subjected to the hydrogenation step in a reactor.

The reactors enabling the hydrogenation are known reactors that are capable of operating under pressure; it may for example be a jacketed reactor. The reactor is generally fitted with a stirrer enabling the homogenization of the reaction medium.

Preferably, the temperature during the hydrogenation step is between 100 and 140° C., most preferentially between 110 and 130° C. Advantageously, the hydrogen pressure in the reactor ranges from 20 to 200 bar, for example from 30 to 100 bar, preferentially from 40 to 60 bar.

At the end of this step, a composition, referred to as prehydrogenated composition, is obtained, which may have a reducing sugar content, determined by the Nelson-Somogyi method, ranging from 0.15 to 1%. The latter is obtained by carrying out the hydrogenation step for a sufficient duration to obtain this reducing sugar content. This duration mainly varies depending on the pressure and temperature conditions used during this step: the higher the pressure and temperature, the shorter the reaction time may be. Nonetheless, those skilled in the art will prefer to use the preferred conditions described above, with a view to only very slightly degrading the structure of the glucose polymer. The duration of this step may range from 90 to 120 minutes, preferably from 120 to 180 minutes.

This prehydrogenated composition may then be subjected to a step of pH modification by adding a base, said composition having a pH ranging from 8.5 to 11, for example from 8.6 to 10, preferentially from 9.10 to 9.90, at the end of this step. The base may be sodium hydroxide.

A step of alkalinization of this prehydrogenated composition is then carried out at a temperature of between 100 and 140° C. for a sufficient duration to form the hydrogenated glucose polymer composition of the invention.

The duration of the alkalinization step mainly varies depending on the temperature conditions used during this step: the higher the temperature and the lower the reducing sugar content of the prehydrogenated composition, the shorter the reaction time may be. Nonetheless, under the conditions indicated, it is preferable to use a duration ranging from 10 to 120 minutes and preferably from 15 to 100 minutes so as to only slightly degrade the structure of the glucose polymer. Surprisingly, this alkalinization step of the process does not degrade, or only slightly degrades, the structure, and does not decrease, or only slightly decreases, the total fiber content of the glucose polymer; without wishing to be bound by any theory, the Applicant hypothesizes that the prehydrogenated composition provided during the hydrogenation step has properties enabling it to be able to be subjected to the alkalinization step without degrading the structure of the glucose polymer. This is particularly essential when the glucose polymer comprises dietary fiber and when it is desired to retain the nutritional advantages of such fiber.

The alkalinization step is also carried out in the presence of a hydrogenation catalyst and hydrogen. The hydrogen pressure may range from 20 to 200 bar, for example from 30 to 100 bar, preferentially from 40 to 60 bar. The alkalinization step may be carried out in the hydrogenation reactor described above, under hydrogen and without separation of the catalyst used during the hydrogenation step, by introducing the base at the end of said hydrogenation step.

Those skilled in the art will be able to vary the parameters of the alkalinization step described above in order to decrease the amount of reducing sugars in the hydrogenated composition of the invention, for example by increasing the temperature or by increasing the duration of this step, or even by increasing the amount of catalyst and by increasing the hydrogen pressure.

The steps of hydrogenation and alkalinization may be of batch or continuous type.

It is possible to withdraw the prehydrogenated composition from the reactor with a view to carrying out the following alkalinization step in another reactor. It is also possible to keep the composition in the same reactor, to carry out the step of modifying the pH therein, then to carry out the alkalinization step.

The catalyst used during the first step or optionally during the second step may be separated from the prehydrogenated composition or the hydrogenated glucose polymer composition by a filtration step, optionally carried out after a decantation step.

The process of the invention may also comprise, following the alkalinization step, a step of purification of the hydrogenated glucose polymer composition. Advantageously, the purification step comprises a step of passing the hydrogenated glucose polymer composition on one or more ion exchange resins. Preferentially, this stage comprises a first pass on a strong cationic resin then a second pass on a weak anionic resin. This stage may also be supplemented by passing on mixed bed. The purification step may also comprise a treatment of the glucose polymer composition with carbon black. The process may also comprise a chromatography step, for example a step of simulated moving bed chromatography.

The composition, still in liquid form at this stage, may be made into solid form. Advantageously, the composition is in the form of a powder which is preferably a spray-dried powder. The process may thus comprise a step of concentration followed by a step of drying. The concentration step may be carried out using any type of evaporator and the drying step may especially be a step of spray drying or a step of granulation. These methods are well known to those skilled in the art.

The hydrogenated glucose polymer composition according to the invention may be used in applications already known for hydrogenated glucose polymers.

The composition according to the invention may especially be used for producing food and pharmaceutical products and especially for the production of beverages, such as non-alcoholic beverages, such as carbonated beverages and especially sodas, tea-based beverages, fruit juices, sugar-free or reduced-sugar beverages, and also alcoholic beverages such as beers, liquors and spirits, for producing dairy products such as yogurts or ice creams, for producing cooked products such as bread, cereals, cakes or cookies, for producing confectionery, for producing jams/jellies or fruit-based preparations, sauces, for producing pasta or noodles, for producing particular nutritional foods such as foods for the elderly or young children or infants, and also dietary supplements which may be in powder or tablet form or else for producing pharmaceutical preparations.

Another subject of the invention relates to the composition according to the invention for producing food products and pharmaceutical products having a pH ranging from 2 to 7.

The invention will now be described in detail in the following examples. It is emphasized that these examples are nonlimiting and in no way able to limit the scope of the present invention.

EXAMPLES

Measurement of Coloration

Coloration is measured according to the ICUMSA method.

After filtration over membrane filter with 0.45 μm porosity (Acrodisc filter), the optical density (OD) at 420 nm of the solution is measured using a spectrophotometer in a 5 cm-long vessel. The brix of the solution is also measured:

$$ICUMSA = \frac{OD * 100000}{Brix * \text{vessel length(cm)} * \text{density}}$$

The coloration of the different hydrogenated glucose polymer compositions is reported in tables 1 and 2 in the "ICUMSA" row.

Method for Determining Stability

A test of the stability of the hydrogenated glucose polymer compositions at different pHs and temperatures is carried out.

The aim is to evaluate the change in coloration over a given time. This makes it possible to characterize the stability of the hydrogenated fibers during a food process.

For this purpose, two solutions of hydrogenated fibers with a solids content of 25% are prepared.

For determining the stability at pH 4 (TEST A), the solution is buffered at pH=4 (Fluka® pH 4 buffer solution comprising citric acid, sodium hydroxide and sodium chloride). For determining the stability at pH 7 (TEST B), the solution is buffered at pH=7 (Fluka® pH 7 buffer solution comprising monopotassium phosphate and disodium phosphate).

The solutions are then placed in closed pyrex test tubes (10 tubes for each pH) and the tubes are placed in an oil bath for 6 hours:

at 115° C. for TEST A, which studies the stability at pH=4;

and at 85° C. for TEST B, which studies the stability at pH=7.

The tubes are then removed from the oil bath and cooled to room temperature (20° C.).

In the same way as above, the coloration according to the ICUMSA method is measured for the different test tubes following the heat treatments, and the mean of the measurements is calculated.

The colorations of the different hydrogenated glucose polymer compositions after treatment are reported in tables 1 and 2 in the "ICUMSA (pH4, 6 h)" and "ICUMSA (pH7, 6 h)" rows.

Example 1A

In a 20 liter jacketed reactor containing Raney nickel in suspension, a glucose polymer of Nutriose® FM 10 type is introduced with stirring.

The Nutriose® FM 10 used comprises approximately 10% of reducing sugars and a fiber content of approximately 74% (AOAC 2001.03), and has a number-average molar mass of 1145 g/mol and a weight-average molar mass of 3480 g/mol.

The solids content of glucose polymer in the reaction medium is 25% by weight, and the Raney nickel content is 5% by weight, expressed relative to the dry weight. The pH of the solution is equal to 5.

The hydrogenation is carried out for 2 h at a pressure of 50 bar hydrogen and a temperature of 120° C.

A prehydrogenated composition is obtained comprising an amount of reducing sugars, determined according to the Nelson-Somogyi method, of 1867 ppm.

A solution of sodium hydroxide at 3% by weight is introduced within 15 minutes so as to bring the pH of the prehydrogenated composition to a value of 9.2 while maintaining the reactor at a pressure of 50 bar hydrogen and a temperature of 120° C. The alkalinization step is then carried out for 15 minutes.

After this time, the reaction is stopped and left to settle for 15 minutes, and the supernatant is decanted to a decanter in order to recover the catalyst. The supernatant from the decanter is then filtered in order to eliminate the final traces of catalyst.

After cooling the syrup obtained in this way to 15° C., it is subjected to purification on strong cationic resin and weak anionic resin, then on mixed bed.

The characteristics of the hydrogenated composition are given in table 1 below.

Example 1B

Example 1B differs from example 1A solely in that the duration of the alkalinization step is 45 minutes instead of 15 minutes.

The characteristics of the hydrogenated composition are given in table 1 below.

Example 1C

Example 1C differs from example 1A solely in that the duration of the alkalinization step is 75 minutes instead of 15 minutes.

The characteristics of the hydrogenated composition are given in table 1 below.

Comparative Example 1

Comparative example 1 (C EX1) differs from example 1A solely in that the duration of the hydrogenation step is 3 h and that no alkalinization step is carried out.

The characteristics of the hydrogenated composition are given in table 2 below.

Example 2A

In a 20 liter jacketed reactor containing Raney nickel in suspension, a glucose polymer of Nutriose® FM06 type is introduced with stirring.

The Nutriose® FM 06 used comprises approximately 5% of reducing sugars and a fiber content of approximately 85% (AOAC 2001.03), and has a number-average molar mass of 2295 g/mol and a weight-average molar mass of 4125 g/mol.

The solids content of glucose polymer in the reaction medium is 25% by weight, and the Raney nickel content is 5% by weight, expressed relative to the dry weight. The pH of the solution is equal to 5.

The hydrogenation is carried out for 3 h at a pressure of 50 bar hydrogen and a temperature of 130° C.

A prehydrogenated composition is obtained comprising an amount of reducing sugars, determined according to the Nelson-Somogyi method, of 1673 ppm.

A solution of sodium hydroxide at 3% by weight is introduced within 15 minutes so as to bring the pH of the prehydrogenated composition to a value of 9.3 while maintaining the reactor at a pressure of 50 bar hydrogen and a temperature of 120° C. The alkalinization step is then carried out for 15 minutes.

After this time, the reaction is stopped and left to settle for 15 minutes, and the supernatant is decanted to a decanter in order to recover the catalyst. The supernatant from the decanter is then filtered in order to eliminate the final traces of catalyst.

After cooling the syrup obtained in this way to 15° C., it is subjected to purification on strong cationic resin and weak anionic resin, then on mixed bed.

The characteristics of the hydrogenated composition are given in table 1 below.

Example 2B

Example 2B differs from example 2A solely in that the duration of the hydrogenation step is 2 h instead of 3 h and in that the duration of the alkalinization step is 75 minutes instead of 15 minutes.

A prehydrogenated composition is obtained comprising an amount of reducing sugars, determined according to the Nelson-Somogyi method, of 3255 ppm. After introducing sodium hydroxide, the pH of the prehydrogenated composition is 9.6.

The characteristics of the hydrogenated composition are given in table 1 below.

Example 2C

Example 2C differs from example 2B solely in that the Raney nickel content is 7.5% by weight expressed relative to dry weight, instead of 5%.

A prehydrogenated composition is obtained comprising an amount of reducing sugars, determined according to the Nelson-Somogyi method, of 2163 ppm. After introducing sodium hydroxide, the pH of the prehydrogenated composition is 9.7.

The characteristics of the hydrogenated composition are given in table 1 below.

Comparative Example 2A

Comparative example 2 A (C EX2 A) differs from example 2C solely in that the duration of the hydrogenation step is 3 h and that no alkalinization step is carried out.

The characteristics of the hydrogenated composition are given in table 2 below.

Comparative Example 2B

Comparative example 2B (C EX2 B) differs from example 2C solely in that the duration of the hydrogenation step is 4 h and that no alkalinization step is carried out.

The characteristics of the hydrogenated composition are given in table 2 below.

Example 3

A glucose polymer composition is provided by reproducing example 1 from application FR 3 032 709 A1.

The composition produced comprises approximately 20.2% of reducing sugars and a fiber content of approximately 61% (AOAC 2001.03), and has a number-average molar mass of 595 g/mol and a weight-average molar mass of 1300 g/mol.

The solids content of glucose polymer in the reaction medium is 25% by weight, and the Raney nickel content is 5% by weight, expressed relative to the dry weight. The pH of the solution is equal to 5.

The hydrogenation is carried out for 2 h at a pressure of 50 bar hydrogen and a temperature of 130° C.

A prehydrogenated composition is obtained comprising an amount of reducing sugars, determined according to the Nelson-Somogyi method, of 1570 ppm.

A solution of sodium hydroxide at 3% by weight is introduced within 15 minutes so as to bring the pH of the prehydrogenated composition to a value of 9.3 while maintaining the reactor at a pressure of 50 bar hydrogen and a temperature of 120° C. The alkalinization step is then carried out for 75 minutes.

After this time, the reaction is stopped and left to settle for 15 minutes, and the supernatant is decanted to a decanter in order to recover the catalyst. The supernatant from the decanter is then filtered in order to eliminate the final traces of catalyst.

After cooling the syrup obtained in this way to 15° C., it is subjected to purification on strong cationic resin and weak anionic resin, then on mixed bed.

The characteristics of the hydrogenated composition are given in table 2 below.

Table 1 also features the characteristics of 2 commercial hydrogenated glucose polymer compositions, Litesse® Ultra which is a hydrogenated polydextrose sold by Danisco or Fibersol® 2H which is a nondigestible dextrin sold by Matsutani.

TABLE 1

Characterization of the hydrogenated glucose polymer compositions

|  | Ex 1A | Ex 1B | Ex 1C | Ex 2A | Ex 2B | Ex 2C | Fibersol® 2H | Litesse® Ultra |
|---|---|---|---|---|---|---|---|---|
| RS | 614 ppm | 370 ppm | 86 ppm | 714 ppm | 391 ppm | 208 ppm | 2501 ppm | 1503 ppm |
| DP1H + DP2H | 4.0 | 4.0 | 4.0 | 0.3 | 0.2 | 0.3 | n.d. | n.d. |
| Mn (g/mol) | 1170 | 1170 | 1170 | 2210 | 2150 | 2170 | 1245 | 715 |
| Mw (g/mol) | 3465 | 3465 | 3415 | 4030 | 3995 | 4000 | 2810 | 1600 |
| Total fiber | 70% | n.d. | 69% | 81% | 80% | 80% | n.d. | 79% |
| ICUMSA | 22 | 15 | 6 | 25 | 18 | 14 | 29 | 28 |
| ICUMSA (pH 4, 6 h) | 62 | 44 | 32 | 87 | 56 | 38 | 154 | 128 |
| ICUMSA (pH 7, 6 h) | 85 | 53 | 41 | 96 | 58 | 47 | 184 | 140 | n.d.: not determined

TABLE 2

Characterization of the hydrogenated glucose polymer compositions

|  | Ex 3 | C Ex 1 | C Ex 2A | C Ex 2B |
|---|---|---|---|---|
| RS | 320 ppm | 1620 ppm | 1150 ppm | 1080 ppm |
| DP1H + DP2H | 20.2 | 4.0 | 0.3 | 0.3 |
| Mn (g/mol) | 595 | 1170 | 2210 | 2210 |
| Mw (g/mol) | 1300 | 3465 | 4030 | 4030 |
| Total fiber | 61% | 70% | 81% | 81% |
| ICUMSA | 25 | 30 | 28 | 28 |
| ICUMSA (pH 4, 6 h) | 29 | 125 | 112 | 105 |
| ICUMSA (pH 7, 6 h) | 39 | 148 | 123 | 116 |

These examples demonstrate the possibility of producing hydrogenated glucose polymer compositions having a very low amount of reducing sugars, much lower than those of the compositions of the prior art.

The comparison between the composition of comparative example 1 and the prehydrogenated composition of example 1A demonstrates that the amount of reducing sugars is not significantly reduced even though the duration was increased by an hour.

The comparison between the composition of comparative example 2A and the prehydrogenated composition of example 2C demonstrates that the amount of reducing sugars, while reduced, is not sufficiently reduced to reach the amount of reducing sugars of the invention, even though the duration was increased by an hour.

The comparison between the composition of comparative example 2B and the composition of comparative example 2A demonstrates that the amount of reducing sugars is not significantly reduced even though the duration was increased by an hour.

Thus, regardless of the conditions selected, only the specific process of the invention, comprising a hydrogenation step and an alkalinization step, made it possible to obtain a hydrogenated glucose polymer composition having a very low amount of reducing sugars, of less than 800 ppm.

The tests also demonstrate that the compositions according to the invention have improved thermal stability at acid or neutral pH. Without wishing to be bound by any theory, this may be explained by the drastic decrease in reducing sugars.

This is a particularly sought-after advantage for a product which will be able to be used in processes for producing food products, since a food product generally has a pH ranging from 2 to 7.

The invention claimed is:

1. A hydrogenated glucose polymer composition, comprising a total fiber content, determined according to the AOAC 2001.03 method, of greater than 50% and an amount of reducing sugars by dry weight RS of less than 800 ppm.

2. The composition according to claim 1, wherein the amount of reducing sugars thereof by dry weight ranges from 20 to 600 ppm.

3. The composition according to claim 1, wherein the glucose polymer is a glucose polymer containing nondigestible dietary fiber.

4. The composition according to claim 3, wherein the total fiber content thereof, determined according to the AOAC 2001.03 method, is greater than 60%.

5. The composition according to claim 1, wherein, relative to the dry weight of the composition, the dry weight of polyols (DP1H+DP2H), resulting from the hydrogenation of the glucose, of the maltose, and of the isomers thereof, is less than 30%.

6. The composition according to claim 1, wherein it has a Mw ranging from 1000 to 6000 g/mol.

7. The composition according to claim 1, wherein it has a Mw of greater than or equal to 2500 g/mol.

8. A process for producing a hydrogenated glucose polymer composition according to claim 1, comprising:
a step of providing an aqueous solution of glucose polymer containing dietary fiber;
a step of bringing the aqueous solution into contact with a hydrogenation catalyst in order to provide, optionally after correcting this pH, a solution having a pH ranging from 4 to 7;
a step of hydrogenation of said solution in a reactor for a sufficient duration to achieve a composition, referred to as prehydrogenated composition, having a reducing sugar content ranging from 0.15 to 1%;
followed by a step of modification of the pH of the prehydrogenated composition by addition of a base, said composition having, at the end of this step, a pH ranging from 8.5 to 11;
followed by a step of alkalinization, also in the presence of a hydrogenation catalyst and hydrogen, of the prehydrogenated composition at a temperature of between 100 and 140° C. for a sufficient duration to form the hydrogenated glucose polymer composition.

9. The process as claimed in claim 8, wherein the hydrogenation step is carried out at a temperature of between 100 and 140° C. and a hydrogen pressure of between 20 and 200 bar.

10. The process according to claim 8, wherein the prehydrogenated composition has a pH, at the end of the pH modification step, ranging from 9.10 to 9.90.

11. The process according to claim 8, wherein, following the alkalinization step, a step of purification of the hydrogenated glucose polymer composition is carried out.

12. The process according to claim 11, wherein the purification step comprises a step of passing the hydrogenated glucose polymer composition on one or more ion exchange resins.

13. The process according to claim 11, wherein the purification step comprises a treatment of the glucose polymer composition with carbon black.

14. The process according to claim 8, further comprising a step of concentration followed by a step of drying.

15. A food or pharmaceutical product, comprising the hydrogenated glucose polymer composition according to claim 1.

16. The composition according to claim 1, wherein the amount of reducing sugars thereof by dry weight ranges from 50 to 400 ppm.

17. The composition according to claim 3, wherein the total fiber content thereof, determined according to the AOAC 2001.03 method, is greater than 70%.

18. The composition according to claim 3, wherein the total fiber content thereof, determined according to the AOAC 2001.03 method, is greater than 80%.

19. The composition according to claim 1, wherein, relative to the dry weight of the composition, the dry weight of polyols (DP1H+DP2H), resulting from the hydrogenation of the glucose, of the maltose, and of the isomers thereof, is less than 25%.

20. The composition according to claim 1, wherein, relative to the dry weight of the composition, the dry weight of polyols (DP1H+DP2H), resulting from the hydrogenation of the glucose, of the maltose, and of the isomers thereof, is less than 15%.

21. The composition according to claim 1, wherein, relative to the dry weight of the composition, the dry weight of polyols (DP1H+DP2H), resulting from the hydrogenation of the glucose, of the maltose, and of the isomers thereof, is less than 5%.

22. The composition according to claim 1, wherein, relative to the dry weight of the composition, the dry weight of polyols (DP1H+DP2H), resulting from the hydrogenation of the glucose, of the maltose, and of the isomers thereof, is less than 2%.

23. The composition according to claim 1, wherein it has a Mw ranging from 1300 to 5000 g/mol.

24. The composition according to claim 1, wherein it has a Mw ranging from 1000 to 3600 g/mol.

25. The composition according to claim 1, wherein it has a Mw ranging from 3600 to 6000 g/mol.

26. The composition according to claim 1, wherein it has a Mw ranging from 2500 to 6000 g/mol.

\* \* \* \* \*